US008673309B2

(12) United States Patent
Nayak

(10) Patent No.: US 8,673,309 B2
(45) Date of Patent: Mar. 18, 2014

(54) METHODS FOR MEASURING HIGH MOLECULAR WEIGHT COMPLEXES OF FIBRINOGEN WITH FIBRONECTIN AND FIBULIN-1

(75) Inventor: Ramesh C. Nayak, Tucson, AZ (US)

(73) Assignee: MSDx, Inc., Tucson, AZ (US)

( * ) Notice: Subject to any disclaimer, the term of this patent is extended or adjusted under 35 U.S.C. 154(b) by 0 days.

(21) Appl. No.: 13/370,757

(22) Filed: Feb. 10, 2012

(65) Prior Publication Data

US 2013/0115631 A1    May 9, 2013

Related U.S. Application Data

(60) Provisional application No. 61/441,903, filed on Feb. 11, 2011.

(51) Int. Cl.
*A61K 38/00* (2006.01)
*A61K 39/395* (2006.01)
*G01N 33/53* (2006.01)
*G01N 33/00* (2006.01)

(52) U.S. Cl.
USPC ............... 424/156.1; 424/130.1; 424/178.1; 435/7.1; 435/7.92; 514/17.7; 514/17.9

(58) Field of Classification Search
None
See application file for complete search history.

(56) References Cited

U.S. PATENT DOCUMENTS

| | | | |
|---|---|---|---|
| 5,578,709 A | 11/1996 | Woiszwillo | |
| 5,874,399 A | 2/1999 | Samal | |
| 6,368,785 B1 | 4/2002 | Ranby | |
| 6,589,746 B1 | 7/2003 | Zemlan | |
| RE38,431 E | 2/2004 | Miekka et al. | |
| 2003/0161826 A1 | 8/2003 | Arnason et al. | |
| 2004/0019118 A1 | 1/2004 | Iqbal et al. | |
| 2007/0048264 A1 | 3/2007 | Kindsvogel et al. | |
| 2007/0072295 A1 | 3/2007 | Slukvin et al. | |
| 2007/0196337 A1 | 8/2007 | Trapani et al. | |
| 2008/0183395 A1 | 7/2008 | Bevilacqua et al. | |

FOREIGN PATENT DOCUMENTS

| | | |
|---|---|---|
| WO | 99/45393 A1 | 9/1999 |
| WO | 02/03073 A1 | 1/2002 |
| WO | 2005/080985 A2 | 9/2005 |

OTHER PUBLICATIONS

Hecker et al. 2011 "reassessment of blood gene expression markers for the prognosis of relapsing-remitting multiple sclerosis" PLoS one 6(12):1-12.*
Chavarria et al. 2002 "maternal plasma cellular fibronectin concentrations in normal and preeclamptic pregnancies: a longitudinal study for early prediction of preeclampsia" Am J Obstet Gynecol 187(3):595-601.*

(Continued)

*Primary Examiner* — Jeffrey Stucker
*Assistant Examiner* — Adam M Weidner

(57) ABSTRACT

A method of detecting MSDX Complex-1, the method introducing a first antibody to a sample to create an antibody-sample mixture, wherein the first antibody is specific for one of fibrinogen, fibronectin, or fibulin-1, the first antibody having a label molecule; providing a well coated with a second antibody, the second antibody is specific for one of fibrinogen, fibronectin, or fibulin-1; introducing the antibody-sample mixture to the well; and introducing a substrate to the antibody-sample mixture in the well, wherein the label molecule and the substrate interact to provide a signal, wherein when the signal is detected then MSDX Complex-1 is detected.

27 Claims, 2 Drawing Sheets

(56) References Cited

OTHER PUBLICATIONS

Grammatikakis et al. 2010 "fibronectin plasma levels in gynecological cancers" J Buon 15(1):122-6.*

Stephens and Vidal-Puig 2006 "an update on visfatin/pre-b cell colony-enhancing factor, an ubiquitously expressed, illusive sytokine that is regulated in obesity" Curr Opin Lipidol 17:128-131.*

Kamiya Biomedical Company 2008 "Mouse Fibronectin ELISA" Cat. No. KT-398. Downloaded from www.kamiyabiomedical.com/pdf/kt-398.pdf on Mar. 5, 2013.*

Adeza Biomedical "fetal fibronectin enzyme immunoassay and rapid fFN for the TLiIQ System". Downloaded from ffntest.com/pdfs/fullterm_product_insert.pdf on Mar. 5, 2013.*

Arnold et al.; Increase in Perforin-positive Peripheral Blood Lymphocytes in Extrinsic and Intrinsic Asthma; Am J Respir Crit Care Med.; vol. 161; p. 182-186; 2000.

Kapaki et al.; Increased Cerebrospinal Fluid Tau Protein in Multiple Sclerosis; Eur Neruol 2000; 43:228-232.

Körner et al.; Molecular Characteristics of Serum Visfatin and Differential Detection by Immunoassays; Journal of Clinical Endocrinology & Metabolism; vol. 92; p. 4783-4791; Sep. 18, 2007.

Dahmen et al.; Elevated Peripheral Visfatin Levels in Narcoleptic Patients; PLoS One; www.plosone.org; vol. 3; p. e2980; Aug. 20, 2008.

Haider et al.; Exercise Traling Lowers Plasma Visfatin Concentrations in Patients with Type 1 Diabetes; Journal of Clinical Endocrinology & Metabolism; vol. 91; p. 4702-4704; Aug. 8, 2006.

Pajvani et al.; Structure-Function Studies of the Adipocyte-secreted Hormone Acrp30/Adiponectin; Journal of Biological Chemistry; vol. 278; p. 9073-9085; Mar. 14, 2003.

Lu et al; Elevated Visfatin/Pre-B-cell Colony-enhancing Factor Plasma Concentration in Ischemic Stroke; Journal of Stroke and Cerebrovascular Diseases; vol. 18, No. 5; p. 354-359; Oct. 2009.

Rukavina et al; Age-Related Decline of Perforin Expression in Human Cytotoxic T Lymphocytes and Natural Killer Cells; Blood Journal; vol. 92; p. 2410-2420; Oct. 1, 1998.

Laterza et al.; Identification of Novel Brain Biomarkers; Neurobiology of Aging; 52:9; p. 1763-1768; 2006.

Laterza et al.; Identification of Novel Brain Biomarkers; Clinical Chemistry; 52:9; p. 1713-1721; 2006.

Galimberti et al.; Serum MCP-1 levels are increased in mild cognitive impairment and mild Alzheimer's disease; Neurobiology of Aging 27 (2006) 1763-1768.

Bomprezzi et al.; Gene expression profile in multiple sclerosis patients and healthy controls: identifying pathways relevant to disease; Human Molecular Genetics; 2003; vol. 12; No. 17; 2191-2199.

Streit et al.; Microglia and neuroinflammation: a pathological perspective; Jounral of Neuroinflammation; Jul. 30, 2004; pp. 1-4.

Bentivolgio et al.; Neuroinflammation and brain infections: Historical context and current perspectives; Brain Research Reviews, 66; 2011; 152-173.

Iglesias et al.; Microarray detection of E2F pathway activation and other targets in multiple sclerosis peripheral blood mononuclear cells; Journal of Neuroimmunology, 150; 2004; 163-177.

Singh et al.; Gene expression changes in peripheral blood mononuclear cells from multiple sclerosis patients undergoing β-interferon therapy; Journal of the neurological Sciences; 258; 2007; 52-59.

Ratts et al.; CD28-CD57+ T cells predominate in CD8 responses to glatiramer acetate; Journal of Neuroimmunology 178; 2006; 117-129.

Rubeša et al.; Increased perforin expression in multiple sclerosis patients during exacerbation of disease in peripheral blood lymphocytes; Journal of Neuroimmunology; 74:198-204; Apr. 1997.

Scherberich et al.; CD14++ Monocytes, CD14+/CD16+ Subset and Soluble CD14 as Biological Markers of Inflammatory Systemic Diseases and Monitoring Immunosuppressive Therapy; Clin Cham Lab Med.; 37(3):209-213; Mar. 1999.

Bartosik-Psujek et al; Tau protein and 14-3-3 are elevated in the cerebrospinal fluid of patients with multiple sclerosis and correlate with intrahecal synthesis of IgG; Journal of Neurology; vol. 251; No. 4; Apr. 2004; pp. 414-420; XP002672838; ISSN: 0340-5354.

Rezai-Zadeh et al.; CNS Infiltration of Peripheral Immune Cells: D-Day for Neurodegenerative Disease?; J Neuroimmune Pharmacol (2009) 4:462-475.

Batrakova et al., A Macophage—Nanozyme Deliver System for Parkinson's Disease; NIH Public Access; Bioconjug Chem. 2007; 18(5): 1498-1506.

Biju et al.; Macrophage-mediated GDNF Delivery Protects Against Dopaminergic Neurodegeneration: A Therapeutic Strategy for Parkinson's Disease; The American Society of Gene & Cell Therapy; www.moleculartherapy.org; vol. 18; No. 8; 1536-1544; Aug. 2010.

Joly et al.; Cooperative Phagocytes—Resident Microglia and Bone Marrow Immigrants Remove Dead Photoreceptors in Retinal Lesions; The American Journal of Pathology 2009; vol. 174; No. 6; 2310-2323.

Guimares et al., Tau protein seems not to be a useful routine clinical marker of axonal damage in multiple sclerosis; Multiple Sclerosis 2006; 12: 354-356.

* cited by examiner

SEQUENCE LISTING

```
<160> NUMBER OF SEQ ID NOS: 3

<210> SEQ ID NO 1
<211> LENGTH: 24
<212> TYPE: PRT
<213> ORGANISM: human

<400> SEQUENCE: 1

Cys Gln Tyr Arg Cys Phe Gln Val Ile Thr Asn Gly Ile Gly Leu Asn
1               5                   10                  15

Leu Phe Lys Asp Pro Val Ala Asp
            20

<210> SEQ ID NO 2
<211> LENGTH: 24
<212> TYPE: PRT
<213> ORGANISM: HUMAN

<400> SEQUENCE: 2

Cys Ser Phe Lys Cys Tyr Ser Val Val Thr Asn Gly Leu Gly Ile Asn
1               5                   10                  15

Val Phe Lys Asp Pro Val Ala Asp
            20

<210> SEQ ID NO 3
<211> LENGTH: 24
<212> TYPE: PRT
<213> ORGANISM: HUMAN

<400> SEQUENCE: 3

Cys Gln Tyr Arg Cys Phe Gln Ile Ile Thr Asn Gly Ile Gly Leu Asn
1               5                   10                  15

Leu Phe Lys Asp Pro Val Ala Asp
            20
```

METHODS FOR MEASURING HIGH MOLECULAR WEIGHT COMPLEXES OF FIBRINOGEN WITH FIBRONECTIN AND FIBULIN-1

CROSS REFERENCE

This application claims priority to U.S. provisional application Ser. No. 61/441,903 filed Feb. 11, 2011, the specification of which is incorporated herein by reference in its entirety.

BACKGROUND OF THE INVENTION

It has been surprisingly discovered that the expression of a protein complex (e.g. an aggregate, a complex) termed "MSDX Complex-1" is elevated in multiple sclerosis patients as compared to healthy controls. MSDX Complex-1 is a high molecule weight complex comprising fibrinogen, fibronectin, and fibulin-1. MSDX Complex-1 alone or in combination with other markers may be useful as an indicator of multiple sclerosis or other diseases or conditions, for example for an inflammatory condition, a neurodegenerative disease or condition, cancer, stroke, or other diseases. MSDx complex-1 alone or in combination with one or more other biomarkers may help monitor disease activity (e.g., relapse, remission, etc.). Monitoring disease activity may be useful for detecting a response (e.g., positive response, negative response, lack of response) to a therapy, for detecting patient compliance with a therapy, or for providing useful clinical information for disease management.

The present invention features methods for measuring high molecular weight complexes of fibrinogen with fibronectin and fibulin-1 ("MSDx Complex-1") and applications thereof. The methods may be used to monitor disease activity and therapeutic efficacy in diseases or conditions that have an inflammatory component, for example autoimmune diseases, neurodegenerative diseases, cancers and metabolic diseases such as type 2 diabetes mellitus. The present invention is not limited to the aforementioned diseases and conditions or the aforementioned applications.

DESCRIPTION OF PREFERRED EMBODIMENTS

Figure 1:
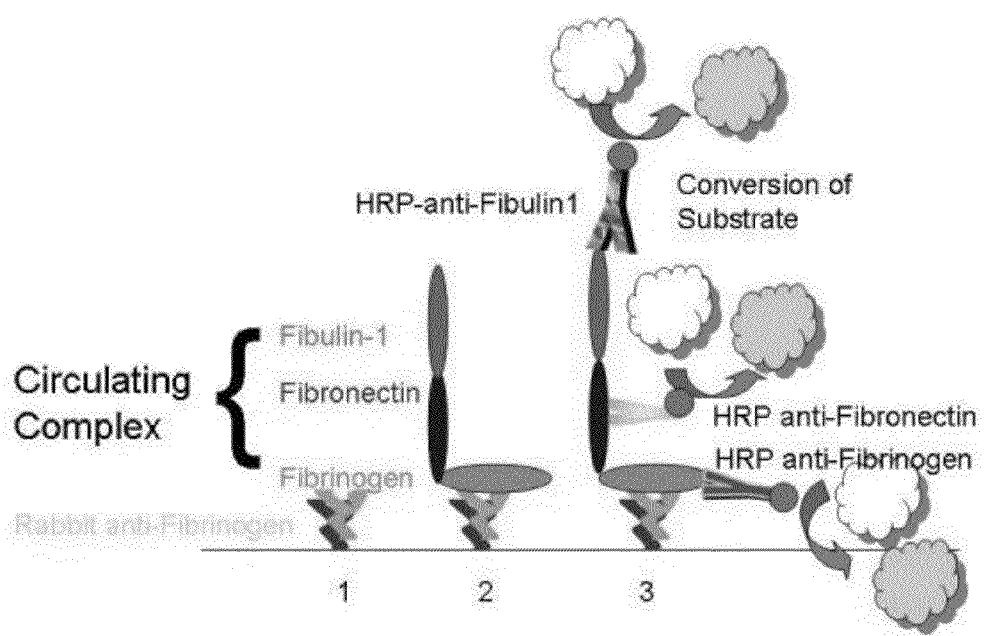
FIG. 1 shows the non-limiting example of a method of detecting MSDX Complex-1 described in EXAMPLE 1.

Referring now to FIG. 1-2, the present invention features methods for measuring high molecular weight complexes of MSDX Complex-1, e.g., fibrinogen with fibronectin and fibulin-1, in a sample. As used herein, the term "MSDx Complex-1" refers to a high molecular weight complex of fibrinogen, fibronectin, and fibulin-1. The detection of MSDX Complex-1 may be used for a variety of purposes, for example for detecting a disease or condition, for monitoring a disease or condition, for monitoring a therapy, etc.

A circulating high molecular weight protein complex has been found to bind certain small peptides selectively. For example, by sephacryl S200 gel filtration chromatography, the binding activity was found in a broad peak of 400,000-900,000 kD. This peak was collected and shown by LC/MS, after in solution protease digestion, to consist of Fibrinogen, Fibronectin and Fibulin-1. The present invention features a unique competitive ELISA assay format to measure the amount of MSDx Complex-1 in a sample, e.g., plasma, by its ability to compete with an anti-peptide antibody for binding of the labeled peptide (e.g., biotinylated peptide). In some embodiments, the method comprises introducing a labeled peptide and an anti-peptide antibody to a sample to create an antibody-sample mixture. The anti-peptide antibody can bind to at least the labeled peptide and MSDX Complex-1. The labeled peptide comprises a label molecule (e.g., biotin). The label molecule is not limited to biotin but may include any appropriate label. Labels are well known to one of ordinary skill in the art.

In some embodiments, the method further comprises providing a well (e.g., ELISA well) coated with a "well antibody". The well antibody is specific for a complex of labeled peptide and anti-peptide antibody. The method further comprises introducing the antibody-sample mixture to the well and introducing a substrate to the antibody-sample mixture in the well. The label molecule of the labeled peptide and the substrate interact to provide a signal. The level of the signal is compared to a control. If the level of the signal is higher than that of the control, then MSDX Complex-1 is not detected. If the level of the signal is lower than that of the control then MSDX Complex-1 is detected.

In some embodiments, the labeled peptide is or comprises SEQ ID NO: 1 (see EXAMPLE 2). In some embodiments, the labeled peptide is or comprises SEQ ID NO: 2 (see EXAMPLE 2). In some embodiments, the labeled peptide is or comprises SEQ ID NO: 3 (see EXAMPLE 2).

In some embodiments, the label of the labeled peptide is located at the C-terminus, the N-terminus or at both termini. In some embodiments, the labeled peptide is between about 15 to 50 amino acids in length, e.g., 24 amino acids, between about 15 to 40 amino acids, between about 15 to 30 amino acids, between about 20 to 30 amino acids, etc. In some embodiments, the labeled peptide has a pI of about 6.1. In some embodiments, the labeled peptide has a pI between about 6 and 7.0, between about 5.5 and 6.5, between about 5.8 and 6.4, etc. In some embodiments, the labeled peptide has a net charge of about −0.1 at pH 7.0. In some embodiments, the labeled peptide comprises an epitope tag disposed at the C-terminus, the N-terminus, or at both termini.

The present invention also features a method of detecting MSDX Complex-1 comprising introducing a first antibody to a sample to create an antibody-sample mixture, wherein the first antibody is specific for one of fibrinogen, fibronectin, or fibulin-1. The first antibody comprises a label molecule (e.g., HRP). A well (e.g., ELISA well) is provided. The well is coated with a second antibody, wherein the second antibody is specific for one of fibrinogen, fibronectin, or fibulin-1. In some embodiments, the method further comprises introducing the antibody-sample mixture to the well and introducing a substrate to the antibody-sample mixture in the well. The label molecule and the substrate interact to provide a signal (e.g., a chemiluminescent signal, a fluorescent signal, a colorimetric signal, a potentiometric signal, an amperometric signal, or a combination thereof). When the signal is detected then MSDX Complex-1 is detected.

In some embodiments, the first antibody is an anti-fibulin-1 antibody and the second antibody is an anti-fibrinogen antibody. In some embodiments, the first antibody is an anti-fibronectin antibody and the second antibody is an anti-fibrinogen antibody. In some embodiments, the first antibody is an anti-fibrinogen antibody and the second antibody is an anti-fibrinogen antibody. In some embodiments, the first antibody is an anti-fibulin-1 antibody and the second antibody is an anti-fibronectin antibody. In some embodiments, the first antibody is an anti-fibronectin antibody and the second antibody is an anti-fibronectin antibody. In some embodiments, the first antibody is an anti-fibrinogen antibody and the second antibody is an anti-fibronectin antibody. In some embodiments, the first antibody is an anti-fibulin-1 antibody and the second antibody is an anti-fibulin-1 antibody. In some embodiments, the first antibody is an anti-fibronectin antibody and the second antibody is an anti-fibulin-1 antibody. In some embodiments, the first antibody is an anti-fibrinogen antibody and the second antibody is an anti-fibulin-1 antibody.

In some embodiments, the method further comprises introducing a third antibody to the antibody-sample mixture prior to introduction to the well, the third antibody is specific for one of fibulin-1, fibronectin, or fibrinogen, wherein the third antibody has a different specificity than the first antibody. In some embodiments, the method further comprises introducing a fourth antibody to the antibody-sample mixture prior to introduction to the well, the third antibody is specific for one of fibulin-1, fibronectin, or fibrinogen, wherein the third antibody has a different specificity than the first antibody and a different specificity than the third antibody.

In some embodiments, the label molecule comprises an enzyme. In some embodiments, the enzyme comprises horseradish peroxidase.

In some embodiments, the first antibody is a rabbit antibody. The first antibody is not limited to rabbit and may be any other appropriate antibody (e.g., mouse, human, etc.). In some embodiments, the second antibody comprises an anti-rabbit antibody, e.g., a goat anti-rabbit antibody, a mouse anti-rabbit antibody, a human anti-rabbit antibody, etc.

As used herein, the term "about" refers to plus or minus 10% of the referenced number.

EXAMPLE 1

The following example describes an example of a method of detecting MSDX Complex-1 according to FIG. 1. Anti-Fibrinogen antibodies are immobilized onto an assay surface (e.g., ELISA well, glass slide, magnetic particle, antibody array matrix) and blocked using conventional methods. A biological fluid (e.g., serum, plasma, cerebrospinal fluid) is then contacted with the immobilized antibody and unbound material is washed off. Then antibodies to fibronectin and/or Fibulin-1 are contacted with the immobilized material and unbound antibodies are washed off. The bound antibodies are then detected with a labelled anti-immunoglobulin of the appropriate specificity to generate a measurable signal (the signal may be chemiluminescent, fluorescent, colorimetric, potentiometric, amperometric etc).

EXAMPLE 2

Figure 2A:
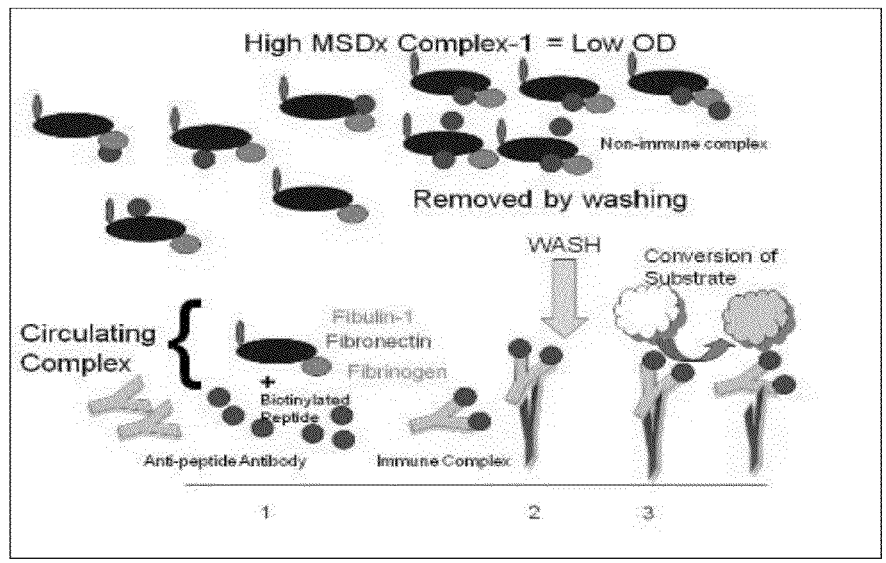
FIG. 2A and FIG. 2B show the non-limiting example of a method of detecting MSDX Complex-1 described in EXAMPLE 2.
Figure 2B:
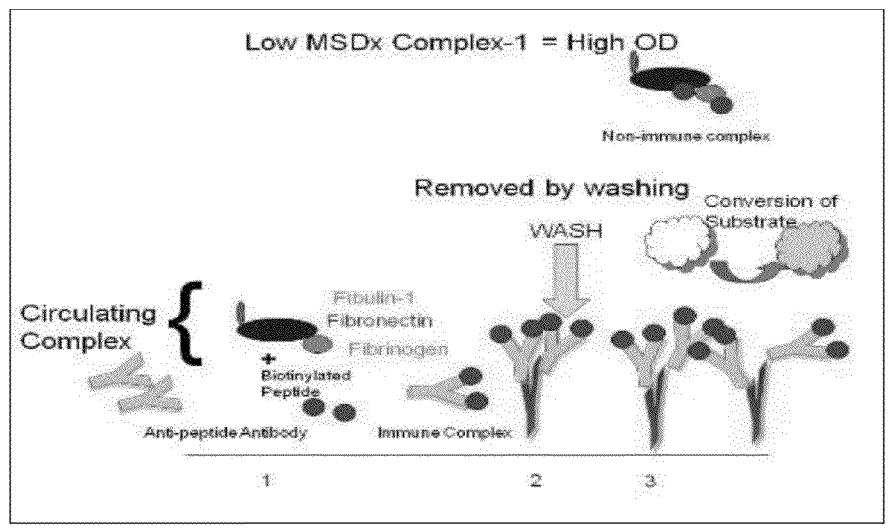

The following example describes an example of a method of detecting MSDX Complex-1 according to FIG. 2A and FIG. 2B. In some embodiments, method is a competitive ELISA assay format. In some embodiments, the competitive ELISA assay used for detecting MDSX Complex-1 utilizes a labeled analyte and measures the ability of an unlabelled native analyte in a biological fluid to compete with the labeled analyte for binding to the antibody. In this assay the labeled analyte is bound by an unrelated binding protein that prevents it's binding to antibody and is washed off before the detection step. A standard curve to quantify binding by MDSX Complex-1 is generated by competition with "cold" peptide.

ELISA wells coated with goat anti-rabbit IgG(Fc) trap immune complexes formed between a rabbit anti-peptide antibody and biotinylated peptide. MSDX Complex-1 in added plasma competes with the rabbit anti-peptide antibody for binding to biotinylated peptide. The more MSDX Complex-1 that is present in the plasma the more biotinylated peptide it binds leaving less available to bind to antibody. Thus high levels of MSDX Complex-1 result in low optical density and vice versa.

In some embodiments, the peptide is labeled at the C-terminal with biotin or another detection agent. In some embodiments, the N-terminal of the peptide may be amine or amide. In some embodiments, the peptide is 24 amino acids long. In some embodiments, the peptide sequence is: CQYRCFQVITNGIGLNLFKDPVAD (SEQ ID NO: 1). In some embodiments, the peptide has a pI of 6.1. In some embodiments, the peptide has a net charge of −0.1 at pH 7.0. In some embodiments, the peptide has an average hydrophilicity (Hopp & Woods method) of −0.3. In some embodiments, the peptide has a ratio of hydrophilic residues to total residues of 33%. In some embodiments, an epitope tag is attached to a terminus, e.g., the N-terminus, to enable the use of other capture antibodies, for example a polyHistidine tag (HisTag).

In some embodiments, any peptide sequence derived by conservative amino acid substitution rules such as the Dayhoff matrix and the like of SEQ ID NO: 1 may be used. In some embodiments, alternative peptides may be used.

In some embodiments, the peptide sequence is CSFKCYSVVTNGLGINVFKDPVAD (SEQ ID NO: 2). In some embodiments, the peptide has a pI of 6.1. In some embodiments, the peptide has a net charge of −0.1 at pH 7.0. In some embodiments, the peptide has an average hydrophilicity (Hopp & Woods method) of −0.3. In some embodiments, the peptide has a ratio of hydrophilic residues to total residues of 33%.

In some embodiments, the peptide sequence is CQYRCFQIITNGIGLNLFKDPVAD (SEQ ID NO: 3). In some embodiments, the peptide has a pI of 6.1. In some embodiments, the peptide has a net charge of −0.1 at pH 7.0. In some embodiments, the peptide has an average hydrophilicity (Hopp & Woods method) of −0.3. In some embodiments, the peptide has a ratio of hydrophilic residues to total residues of 33%.

The various peptides described bind selectively to a macromolecular complex consisting of Fibrinogen B, Fibronectin and Fibulin 1. The levels of this complex have surprisingly been found to be associated with neuroinflammatory diseases including multiple sclerosis. Addition of the peptide to plasma or serum causes the peptide to bind to the complex of Fibrinogen B, Fibronectin and Fibulin 1 effecting a transformation of matter that results in the formation of the aggrefatin complex.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of detecting MSDX Complex-1, the method comprises:
   (a) introducing a first antibody to a sample to create an antibody-sample mixture, wherein the first antibody is specific for a target molecule, the target molecule comprising fibrinogen, fibronectin, or fibulin-1, the first antibody comprises a label molecule;
   (b) providing a well coated with a second antibody, the second antibody is specific for one of the target molecules for which the first antibody is not specific;
   (c) introducing the antibody-sample mixture to the well; and
   (d) introducing a substrate to the antibody-sample mixture in the well, wherein the label molecule and the substrate interact to provide a signal, wherein when the signal is detected then MSDX Complex-1 is detected.

2. The method of claim 1, wherein the sample comprises a circulating phagocyte.

3. The method of claim 1, wherein the sample comprises serum, plasma, peripheral blood mononuclear cells (PBMCs), or a combination thereof.

4. The method of claim 1, wherein the first antibody is an anti-fibulin-1 antibody and the second antibody is an anti-fibrinogen antibody.

5. The method of claim 1, wherein the first antibody is an anti-fibronectin antibody and the second antibody is an anti-fibrinogen antibody.

6. The method of claim 1, wherein the first antibody is an anti-fibulin-1 antibody and the second antibody is an anti-fibronectin antibody.

7. The method of claim 1, wherein the first antibody is an anti-fibrinogen antibody and the second antibody is an anti-fibronectin antibody.

8. The method of claim 1, wherein the first antibody is an anti-fibronectin antibody and the second antibody is an anti-fibulin-1 antibody.

9. The method of claim 1, wherein the first antibody is an anti-fibrinogen antibody and the second antibody is an anti-fibulin-1 antibody.

10. The method of claim 1, wherein the label molecule comprises an enzyme.

11. The method of claim 10, wherein the enzyme comprises horseradish peroxidase.

12. The method of claim 1, wherein the signal is a chemiluminescent signal, a fluorescent signal, a colorimetric signal, a potentiometric signal, an amperometric signal, or a combination thereof.

13. A method of detecting MSDX Complex-1, the method comprises:
   (a) introducing a labeled peptide and an anti-peptide antibody to a sample to create an antibody-sample mixture, the anti-peptide antibody can bind to at least the labeled peptide and MSDX Complex-1, the labeled peptide comprises a label molecule;

(b) providing a well coated with a well antibody, the well antibody is specific for a complex of labeled peptide and anti-peptide antibody;
(c) introducing the antibody-sample mixture to the well; and
(d) introducing a substrate to the antibody-sample mixture in the well, wherein the label molecule of the labeled peptide and the substrate interact to provide a level of a signal; and
(e) comparing the level of the signal to a control, wherein if the level of the signal is higher than that of the control then MSDX Complex-1 is lower than that in the control, wherein if the level of the signal is lower than that of the control then MSDX Complex-1 is higher than that in the control and MSDX Complex-1 is detected.

14. The method of claim 13, wherein the label molecule is biotin.

15. The method of claim 13, wherein the labeled peptide comprises at least SEQ ID NO: 1.

16. The method of claim 13, wherein the labeled peptide comprises at least SEQ ID NO: 2.

17. The method of claim 13, wherein the labeled peptide comprises at least SEQ ID NO: 3.

18. The method of claim 13, wherein the label molecule of the labeled peptide is located at the C-terminus, the N-terminus or at both termini.

19. The method of claim 13, wherein the labeled peptide is between about 15 to 50 amino acids in length.

20. The method of claim 13, wherein the labeled peptide has a pI of about 6.1.

21. The method of claim 13, wherein the labeled peptide has a net charge of about −0.1 at pH 7.0.

22. The method of claim 13, wherein the labeled peptide comprises an epitope tag disposed at the C-terminus, the N-terminus, or at both termini.

23. The method of claim 13, wherein the sample comprises a circulating phagocyte.

24. The method of claim 13, wherein the sample comprises serum, plasma, peripheral blood mononuclear cells (PBMCs), or a combination thereof.

25. A method of detecting Multiple Sclerosis in a patient, the method comprises:
(a) obtaining from a patient a fluid sample from outside of a brain tissue of the patient, the fluid sample comprises peripheral blood mononuclear cells (PBMCs); and
(b) detecting MSDX Complex-1 in the fluid sample, wherein MSDX Complex-1 is a protein complex comprising fibrinogen, fibronectin, and fibulin-1, when MSDX Complex-1 is detected then Multiple Sclerosis is detected in the patient.

26. The method of claim 25, wherein the fluid sample comprises a circulating phagocyte.

27. The method of claim 26, wherein the circulating phagocyte includes a monocyte, a macrophage, or a lymphocyte.

* * * * *